(12) United States Patent
Modha et al.

(10) Patent No.: US 10,870,527 B2
(45) Date of Patent: Dec. 22, 2020

(54) GLOVE DISPENSING ASSEMBLY

(71) Applicant: O&M Halyard, Inc., Mechanicsville, VA (US)

(72) Inventors: Shantilal Hirjibhai Modha, Milton, GA (US); Tantima Saelim, Songkhla (TH)

(73) Assignee: O&M Halyard, Inc., Mechanicsville, VA (US)

( * ) Notice: Subject to any disclaimer, the term of this patent is extended or adjusted under 35 U.S.C. 154(b) by 0 days.

(21) Appl. No.: 15/570,020

(22) PCT Filed: Apr. 7, 2016

(86) PCT No.: PCT/US2016/026364
§ 371 (c)(1),
(2) Date: Oct. 27, 2017

(87) PCT Pub. No.: WO2016/176016
PCT Pub. Date: Nov. 3, 2016

(65) Prior Publication Data
US 2018/0162628 A1 Jun. 14, 2018

Related U.S. Application Data

(60) Provisional application No. 62/155,238, filed on Apr. 30, 2015.

(51) Int. Cl.
*B65D 83/08* (2006.01)
*A61B 42/40* (2016.01)

(52) U.S. Cl.
CPC .......... *B65D 83/0817* (2013.01); *A61B 42/40* (2016.02)

(58) Field of Classification Search
CPC ............................ B65D 83/0817; A61B 42/40
(Continued)

(56) References Cited

U.S. PATENT DOCUMENTS 281,354 A 7/1883 Edwards
466,792 A 1/1892 Lindemeyer
(Continued)

FOREIGN PATENT DOCUMENTS

CN 201890395 U 7/2011
DE 20316963 U1 3/2005
(Continued)

OTHER PUBLICATIONS

International Search Report for PCT/US2016/026364, dated Jun. 17, 2016, 3 pages.

*Primary Examiner* — Rakesh Kumar
(74) *Attorney, Agent, or Firm* — Dority & Manning, P.A.

(57) ABSTRACT

The present disclosure is directed to a dispensing assembly for dispensing articles, such as disposable gloves, and methods of manufacturing same. The dispensing assembly includes a container having a plurality of exterior panels. The exterior panels define an internal chamber and an dispenser opening on the container. The dispensing assembly also includes an article dispensing component housed within the internal chamber. The article dispensing component includes a first panel and a second panel configured together to form an article storage area. The article storage area is configured to receive a plurality of articles. In addition, the first panel is stationary and the second panel is biased towards the first panel via one or more flexible members. Further, the first and second panels include one or more aligned recesses configured to receive the one or more flexible members. Thus, the second panel is configured to maintain the articles adjacent to the dispenser opening of the container as the articles are dispensed from the opening of the container.

14 Claims, 5 Drawing Sheets

(58) Field of Classification Search
USPC .... 221/197, 46, 63, 36, 34, 35, 52, 254, 59, 221/279, 58, 56; 206/494
See application file for complete search history.

(56) References Cited

U.S. PATENT DOCUMENTS

| | | | |
|---|---|---|---|
| 537,613 A | 4/1895 | Lucas | |
| 1,218,196 A | 3/1917 | McCorkindale | |
| 1,707,578 A * | 4/1929 | Shaffer | A47K 10/422 221/62 |
| 2,011,403 A | 8/1935 | Gessler | |
| 2,267,305 A | 12/1941 | Natwick et al. | |
| 2,509,841 A * | 5/1950 | Rose | B42F 21/00 283/40 |
| 2,634,855 A * | 4/1953 | Mandel | B65D 83/0817 221/59 |
| 2,937,742 A | 5/1960 | Michiel | |
| 3,197,062 A | 7/1965 | Day | |
| 3,202,316 A * | 8/1965 | Silver | B65D 83/0817 221/59 |
| 3,313,583 A * | 4/1967 | Turkington | A47K 10/24 312/61 |
| 3,647,114 A * | 3/1972 | Bleuer | A47K 10/422 221/59 |
| 3,746,152 A | 7/1973 | Allen | |
| 3,765,565 A * | 10/1973 | Fietzer | A47K 10/427 221/46 |
| 3,942,682 A * | 3/1976 | McKay | A47K 10/422 221/58 |
| 4,158,412 A | 6/1979 | Wysocki | |
| 4,281,259 A | 7/1981 | Ozawa | |
| 4,407,473 A | 10/1983 | Howe, Jr. | |
| 4,616,767 A * | 10/1986 | Seido | A47K 10/421 221/58 |
| 4,913,312 A | 4/1990 | Boutin | |
| 4,997,105 A * | 3/1991 | Fischer | B65D 5/16 206/278 |
| 5,161,702 A | 11/1992 | Skalski | |
| 5,197,631 A | 3/1993 | Mishima | |
| 5,363,985 A | 11/1994 | Cornell | |
| 5,507,428 A | 4/1996 | Robinson, Jr. et al. | |
| 5,803,345 A | 9/1998 | Jones et al. | |
| 5,897,023 A | 4/1999 | Lee | |
| 5,921,434 A | 7/1999 | Hollander et al. | |
| 5,979,700 A * | 11/1999 | Suess | B65D 83/0817 221/52 |
| 5,992,683 A * | 11/1999 | Sigl | A47K 10/422 221/52 |
| 6,112,936 A | 9/2000 | Arizmendi | |
| 6,189,730 B1 * | 2/2001 | McClymonds | A47K 10/3818 221/197 |
| 6,488,175 B2 | 12/2002 | Shiffler et al. | |
| 6,543,642 B1 * | 4/2003 | Milliorn | B65D 77/06 206/438 |
| 6,749,084 B2 * | 6/2004 | Thompson | B42D 5/005 221/56 |
| 6,886,714 B2 | 5/2005 | Kruchoski et al. | |
| 6,997,310 B1 * | 2/2006 | Fenley | B42F 7/145 206/214 |
| 7,481,313 B1 | 1/2009 | Kramedjian et al. | |
| 7,699,189 B2 * | 4/2010 | Tramontina | B65D 83/0817 221/36 |
| 7,708,154 B2 * | 5/2010 | Lang | A47F 1/126 211/59.3 |
| 7,735,679 B2 * | 6/2010 | Liu | B65H 3/54 221/307 |
| 7,806,291 B2 * | 10/2010 | Anderson | A47K 10/3818 221/33 |
| 8,646,653 B2 | 2/2014 | Lien et al. | |
| 8,650,842 B2 | 2/2014 | Stollery et al. | |
| 2003/0116580 A1 * | 6/2003 | Baughman | A61B 42/40 221/45 |
| 2003/0201276 A1 * | 10/2003 | Fuller | B65D 83/0805 221/155 |
| 2004/0169047 A1 * | 9/2004 | Behnke | B65D 83/0817 221/45 |
| 2006/0273102 A1 * | 12/2006 | Wieser | A47K 10/422 221/59 |
| 2007/0210096 A1 | 9/2007 | Ellswood et al. | |
| 2007/0215630 A1 | 9/2007 | Tramontina | |
| 2008/0164276 A1 | 7/2008 | Kan | |
| 2008/0314777 A1 * | 12/2008 | Foster | G09F 3/20 206/223 |
| 2009/0057172 A1 | 3/2009 | Hungler et al. | |
| 2009/0090736 A1 | 4/2009 | Cowell et al. | |
| 2012/0037577 A1 * | 2/2012 | Wootten, Jr. | A47F 7/18 211/45 |
| 2012/0118905 A1 * | 5/2012 | Lindbergh | A47K 10/421 221/1 |
| 2012/0279981 A1 | 11/2012 | Thomas et al. | |
| 2012/0298689 A1 * | 11/2012 | Cohen | A61B 42/40 221/197 |
| 2013/0164729 A1 * | 6/2013 | Rappa | G09B 19/02 434/365 |
| 2013/0186800 A1 * | 7/2013 | Lien | B65D 5/542 206/526 |
| 2013/0239449 A1 * | 9/2013 | Heinrichs | G09F 3/04 40/665 |
| 2015/0232216 A1 * | 8/2015 | Stollery | B65B 25/20 53/436 |
| 2018/0162628 A1 * | 6/2018 | Modha | B65D 83/0817 |

FOREIGN PATENT DOCUMENTS

| | | | |
|---|---|---|---|
| DE | 102004015576 A1 | 11/2005 | |
| DE | 102005056162 A1 * | 7/2007 | B65D 5/5213 |
| DE | 102005056162 A1 | 7/2007 | |
| EP | 3020655 A1 * | 5/2016 | B65D 5/725 |
| GB | 2385314 A | 8/2000 | |
| GB | 2385314 A * | 2/2001 | B65D 33/00 |
| GB | 2385314 A * | 8/2003 | B65D 33/001 |
| GB | 2467234 A | 7/2010 | |
| GB | 24985023 * | 4/2011 | A61B 19/04 |
| GB | 2489326 A | 9/2012 | |
| GB | 2495023 A * | 3/2013 | B65D 5/545 |
| GB | 2495023 A | 3/2013 | |
| GB | 2503677 A | 1/2014 | |
| GB | 2519839 A | 5/2015 | |
| JP | S62271870 A | 11/1987 | |
| JP | H07291372 A | 11/1995 | |
| JP | H09315469 A | 12/1997 | |
| NL | 6703027 A | 5/1968 | |
| WO | WO 03/078272 A1 | 9/2003 | |
| WO | WO 2006/000242 A1 | 1/2006 | |
| WO | WO 2014/140573 A1 | 9/2014 | |

* cited by examiner

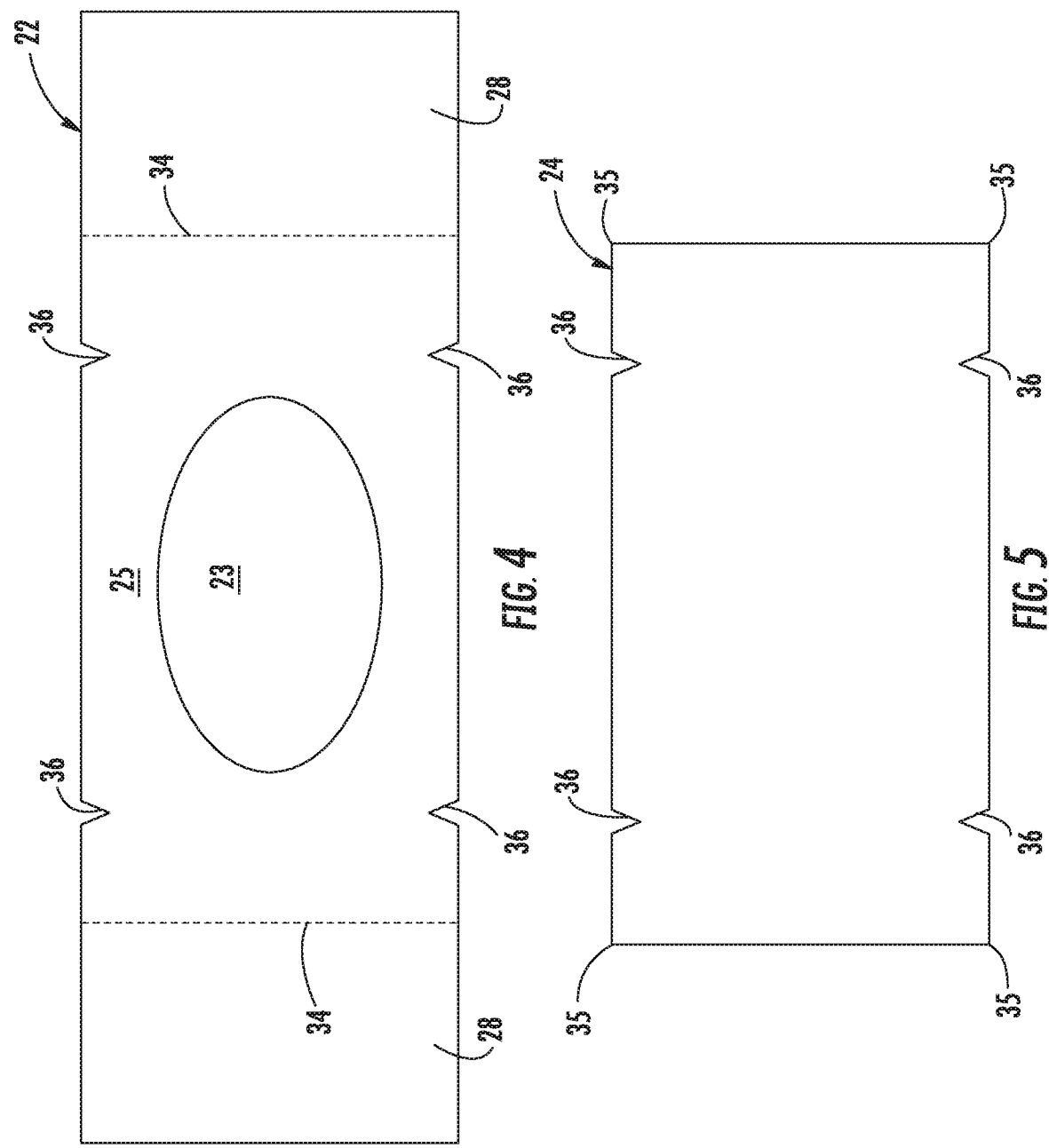

GLOVE DISPENSING ASSEMBLY

RELATED APPLICATIONS

The present application claims priority to U.S. Provisional Application Ser. No. 62/155,238 filed on Apr. 30, 2015 and International Application Number PCT/US2016/026364 filed on Apr. 7, 2016, which is incorporated herein in its entirety by reference hereto.

FIELD OF THE INVENTION

The present invention relates in general to a dispensing assembly, and more particularly to a glove dispensing assembly and methods of making same.

BACKGROUND OF THE INVENTION

A variety of single use, disposable products such as gloves, facemasks and the like are packaged in dispensing cartons. These dispensing cartons frequently have an opening or dispensing orifice cover.

Exemplary cartons or carton modifications for dispensing a variety of products including surgical gloves, tissues, dust mitts, and disposable gloves, are described at, for example:

U.S. Pat. No. 3,746,152 for "Surgical Glove Carton" issued to Allen on Jul. 17, 1973, describes a flat, sterilizable carton that is configured to store a pair of surgical gloves for an extended period in sterile condition and then "snap open" to a flat configuration and also lock in the flat configuration to present the surgical gloves to a user on a sterile field of cardboard.

U.S. Pat. No. 6,112,936 for "Medical Glove Dispensing Enclosure" issued to Arizmendi on Sep. 5, 2000, describes an envelope made of tubular net material that is stretched around a glove dispensing box or the like such that a sphincter closure in the net material is located over an opening in the dispensing box. The sphincter closure is made by cutting a hole in the net material and weaving an elastic band around the hole.

U.S. Pat. No. 6,488,175 for "Dusting Mitt Dispensing System" issued to Shiffler et al., on Dec. 3, 2002, describes a dispensing system for dispensing dusting mitts that have a thumb that is folded and arranged to present the thumb at the top of a stack of mitts. The dispensing system includes a carton having a top cover that pivots along a top seam at the back of the carton. The top cover contains a perforation pattern that forms an access flap when the perforations are severed. The access flap is integrally connected to the top cover along a seam to provide access to the contents.

U.S. Pat. No. 6,886,714 for "Container Allowing Choice of Multiple Openings for Dispensing Preference" issued to Kruchoski et al., on May 3, 2005, describes a dispensing container for dispensing sheets in which the container has a first dispensing opening for pop-up dispensing of sheets such as facial tissue. The container has a second opening to provide group dispensing of a plurality of sheets simultaneously without having to disassociate the sheets from each other. The openings can be overlaid on each other, or one opening can be placed on one portion of the container and another opening on another portion of the container to provide a consumer with various dispensing options.

U.S. Patent Application Publication No.: 2007/0210096 A1 for "High-Volume Package Dispense" by Ellswood et al., published on May 3, 2005, describes a dispenser package system for protective articles, having a substantially vertical product storage orientation and package design. The package includes a double or multi-chambered dispenser unit that can provide within substantially the same footprint as a conventional dispenser container a greater volume of product. The package can store and dispense at least 50 percent, up to about 200 percent or greater capacity than conventional dispenser for protective article products such as gloves or face masks.

Thus, the art is continuously seeking new and improved dispensing assemblies for dispensing a variety of products. More specifically, assemblies that effectively dispense individual products, e.g. examination gloves, as the quantity of products become depleted to a level that the products are no longer located near the dispenser opening would be welcomed in the art. The need for such assemblies is particularly apparent for larger volume packages having contents that may settle or become difficult to access, particularly in a health care environment.

BRIEF SUMMARY OF THE INVENTION

Aspects and advantages of the invention will be set forth in part in the following description, or may be obvious from the description, or may be learned through practice of the invention.

In one aspect, the present disclosure is directed to a dispensing assembly for dispensing articles such as disposable gloves. The dispensing assembly includes a container having a plurality of exterior panels. The exterior panels define an internal chamber and an opening on the container. The dispensing assembly also includes an article dispensing component housed within the internal chamber. The article dispensing component includes a first panel and a second panel configured together to form an article storage area. The article storage area is configured to receive a plurality of articles. In addition, the first panel is stationary and the second panel is biased towards the first panel via one or more flexible members. Further, the first and second panels include one or more aligned recesses configured to receive the one or more flexible members.

In one embodiment, the first panel of the article dispensing component is fixed to a top panel of the container. In another embodiment, the article dispensing component is sized so as to provide an interference fit within the internal chamber of the container.

In further embodiments, the flexible members are configured to allow movement of the second panel toward to the first panel as each article is dispensed from the opening. In certain embodiments, the second panel may include sharp corners or rounded corners.

In particular embodiments, the flexible members may include elastic, e.g. rubber, bands configured circumferentially around the article dispensing component and within the aligned recesses of the first and second panels. In further embodiments, the flexible members may include any suitable members configured to bias the second panel towards the first panel, e.g. a spring.

In yet another embodiment, the first panel includes an orifice that aligns with the opening of the container. In further embodiments, the first panel may also include one or more end flaps configured to form one or more side edges of the article storage area. More specifically, in certain embodiments, the one or more end flaps may be integral with the first panel. Alternatively, the end flaps may be separate from the first panel and attached to the first and second panels to form the side edges.

In still further embodiments, the exterior panels of the container may also include opposing side panels and opposing end panels. Thus, either or both of the side panels or the end panels may be configured to open, thereby allowing insertion or removal of the article dispensing component. Further, it should be understood that the articles as described herein may include any suitable articles, including but not limited to gloves, facemasks, paper products (e.g. tissues, paper towels, etc.) dust mitts, or similar.

In another aspect, the present disclosure is directed to a method for manufacturing a dispensing assembly. The method includes providing a first panel and a second panel. Another step includes placing a plurality of articles on the second panel and then placing the first panel atop the plurality of articles to form an article storage area. The method also includes securing, via one or more flexible members, the first and second panels together to form an article dispensing component. Thus, the flexible members provide a bias of the second panel towards the first panel. Next, the method includes inserting the article dispensing component into a container having a plurality of exterior panels. It should be understood that the method may further include any of the additional steps and/or features as described herein.

In yet another aspect, the present disclosure is directed to a package of articles. The package of articles includes a container having at least a top panel and a bottom panel defining an internal chamber. Further, the top panel has at least one opening. The package of articles also includes an article dispensing component housed within the internal chamber. The article dispensing component includes a first panel and a second panel. Further, the second panel is configured to move relative to the first panel as each article is dispensed from the opening. It should be understood that the package of articles may further include any of the additional features as described herein.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 4 illustrates a top view of one embodiment of a first or top panel of a dispensing assembly according to the present disclosure;

FIG. 5 illustrates a top view of one embodiment of a second or bottom panel of a dispensing assembly according to the present disclosure;

DETAILED DESCRIPTION

Figure 1:
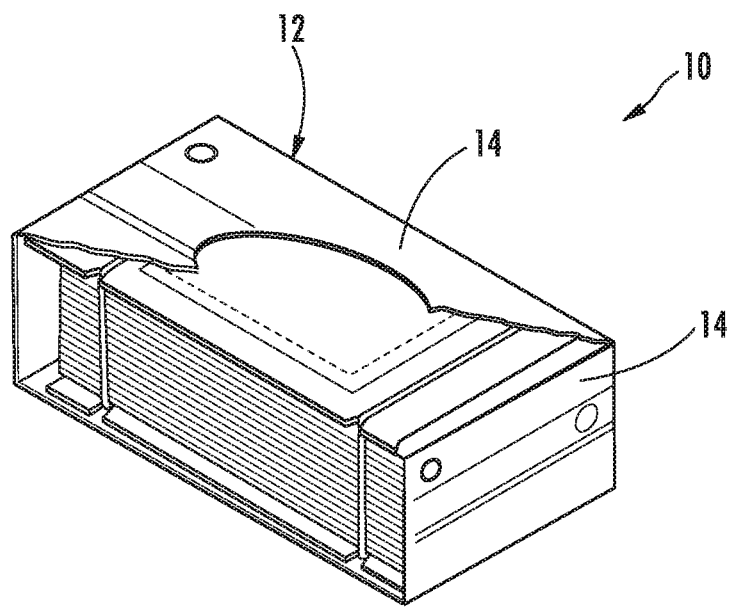
FIG. 1 illustrates a perspective view of one embodiment of a dispensing assembly for dispensing articles, such as disposable gloves, according to the present disclosure.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Figure 2:
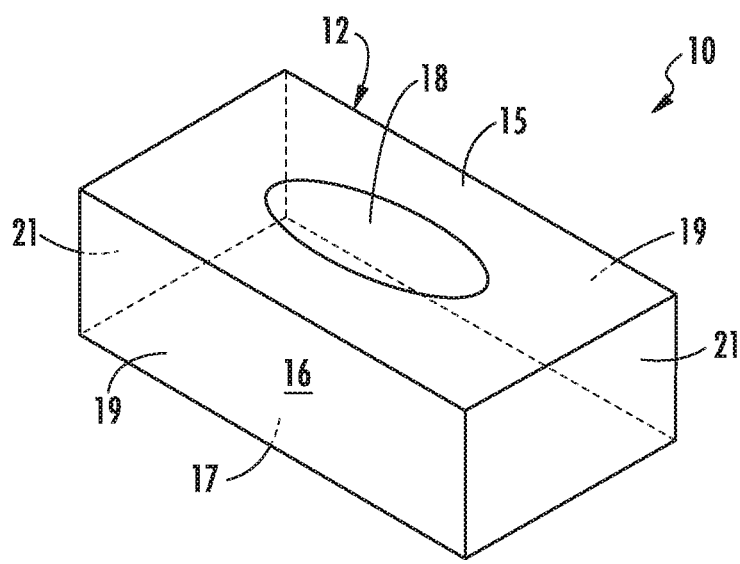
FIG. 2 illustrates a perspective view of one embodiment of a container of a dispensing assembly according to the present disclosure.

Referring now to the drawings, FIG. 1 illustrates a perspective, cut-away view of an exemplary dispensing assembly 10 or package for dispensing articles such as, for example, disposable examination gloves, facemasks, paper products (e.g. tissues, paper towels, etc.) dust mitts, or the like. As shown, the dispensing assembly 10 includes a container 12 having a plurality of exterior panels 14. The exterior panels 14 may be constructed of any suitable material such as, for example, carton cardboard stock, paperboard, heavy structural paper, container stock, corrugated paperboard, plastic coated paper, plastic sheets, wax-coated papers or the like, and combinations thereof. Further, as shown in FIG. 2, the exterior panels 14 of the container 12 define an internal chamber 16 and an opening 18 on the container 12 for dispensing articles therethrough. More specifically, as shown, the exterior panels 14 include a top panel 15, a bottom panel 17, opposing side panels 19, and opposing end panels 21. Thus, in certain embodiments, either or both of the side panels 19 or the end panels 21 may be configured to open, thereby allowing insertion or removal of a plurality of articles as described herein. In further embodiments, certain panels of the container 12 may be excluded, for example, the side panels, or any other suitable combination.

In addition, as shown, the opening 18 has a generally oval shape, however, it should be understood that the opening 18 may have any other suitable shape such that one or more articles can be dispensed therethrough. Further, the opening 18 may include a removable section defined by perforations, scores, underscores, or partial cuts through the material and combinations thereof. Such features are known to those of ordinary skill in the art. For example, U.S. Pat. No. 4,158, 412 for "Tear Out Opening Device" issued to Wysocki on Jun. 19, 1979, describes half-cut configurations used for a tear out flap, the contents of which are incorporated herein by reference in its entirety. In addition, the opening 18 may be configured according to U.S. Pat. No. 8,646,653 entitled "Dispensing Assembly and Package of Articles" which is incorporated herein by reference in its entirety.

Figure 3:
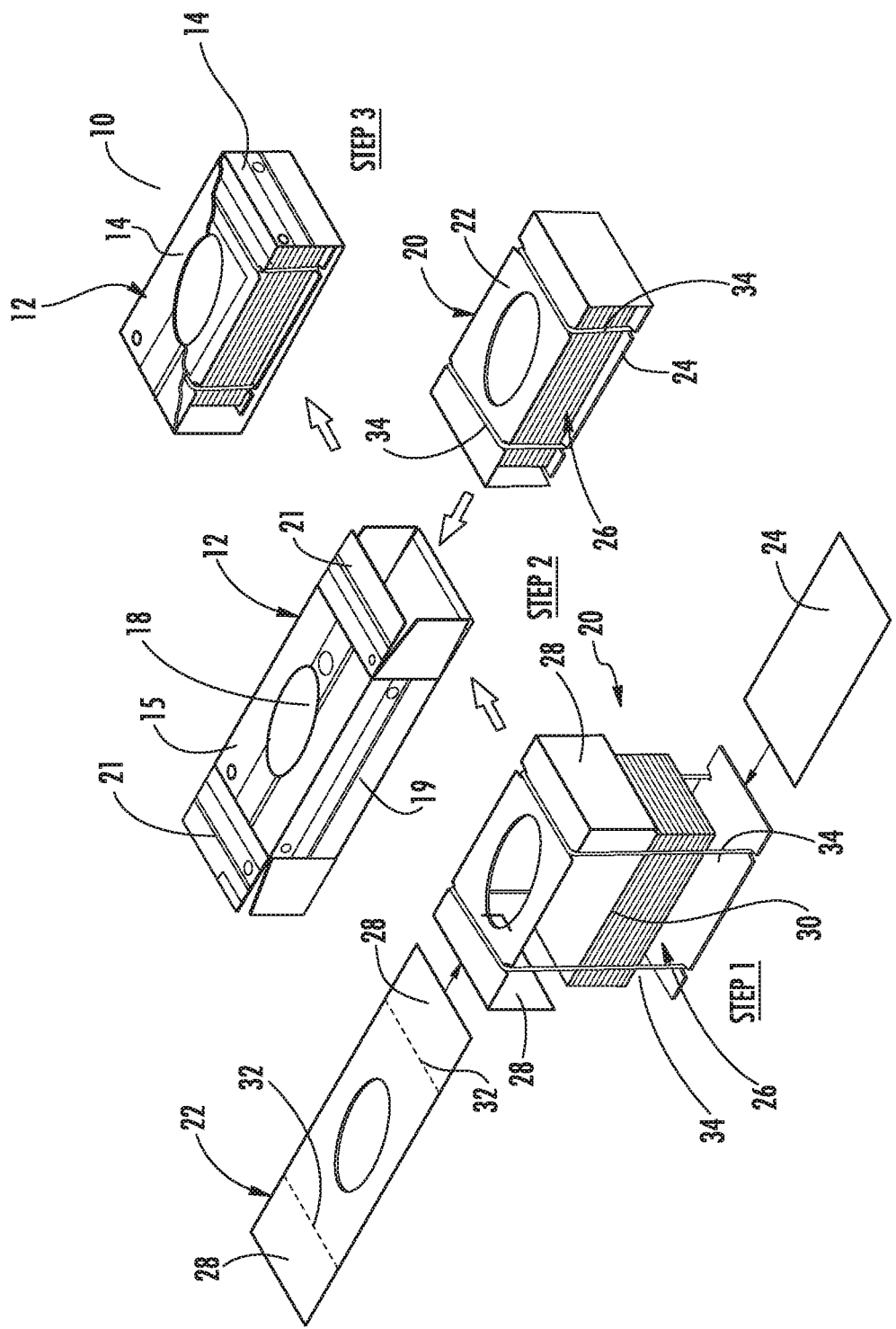
FIG. 3 illustrates a schematic diagram of one embodiment of a process of manufacturing a dispensing assembly according to the present disclosure.

Referring now to FIG. 3, the dispensing assembly 10 also includes an article dispensing component 20 housed within the internal chamber 16. More specifically, FIG. 3 illustrates various steps of assembling the dispensing assembly 10 according to one embodiment of the present disclosure. As shown at STEP 1, the article dispensing component 20 includes a first panel 22 and a second panel 24 configured together to form an article storage area 26. Thus, the article storage area 26 is configured to receive a plurality of articles 30 therein. More specifically, as shown in the illustrated embodiment, the second panel 24 forms the bottom of the article storage area 26 and the top panel 22 forms the top of the article storage area 26. In addition, the first panel 22 includes an orifice 23 that aligns with the opening 18 of the container 12 when the article dispensing component 20 is within the internal chamber 16. More specifically, in certain embodiments, the orifice 23 of the top panel 22 is configured to align with the opening 18 of the container 12 regardless of which direction the article dispensing component 20 is inserted into the container 12 (i.e. regardless of which end of the article dispensing component 20 is inserted into the container 12 first). As such, the article dispensing component 20 fits universally within the container 12 to simplify the manufacturing process.

Referring particularly to FIGS. 3 and 4, the first panel 22 may include one or more end flaps 28 configured to form one or more side edges of the article storage area 26. In certain embodiments, the end flaps 28 may be integral with the first panel 22. For example, as shown, the first panel 22 may be constructed of a unitary piece of material divided into multiple parts via one or more seams 32. Thus, the first panel 22 may include a center portion 25 with opposing end flaps 28 that form the side edges of the article dispensing component 20. Alternatively, the end flaps 28 may be separate and detached pieces of material from the first panel 22. In such embodiments, the end flaps 28 may be joined to the first panel 22 via any suitable means, including but not limited to adhesive or tape.

In additional embodiments, the center portion 25 of the first panel 22 may have generally the same dimensions as the second panel 24. Thus, in such an embodiment, the article dispensing component 20 (i.e. formed by the first and second panels 22, 24) may have a generally square or rectangular shape when assembled.

Referring generally to the figures, the first panel 22 of the article dispensing component 20 may be stationary and the second panel 24 may be biased towards the first panel 22. In other words, the second panel 24 may be configured to move relative to the first panel 22 as each article (e.g. glove) is dispensed from the opening 18 of the container 12. More specifically, in certain embodiments, the first panel 22 may be fixed to the top panel 15 of the container 12. In alternative embodiments, the article dispensing component 20 may be sized so as to provide an interference fit within the internal chamber 16 of the container 12. Thus, the first panel 22 does not have to be fixed to the top panel 15, but rather, simply remains stationary by abutting against an interior surface of the top panel 15 of the container 12.

Figure 6:
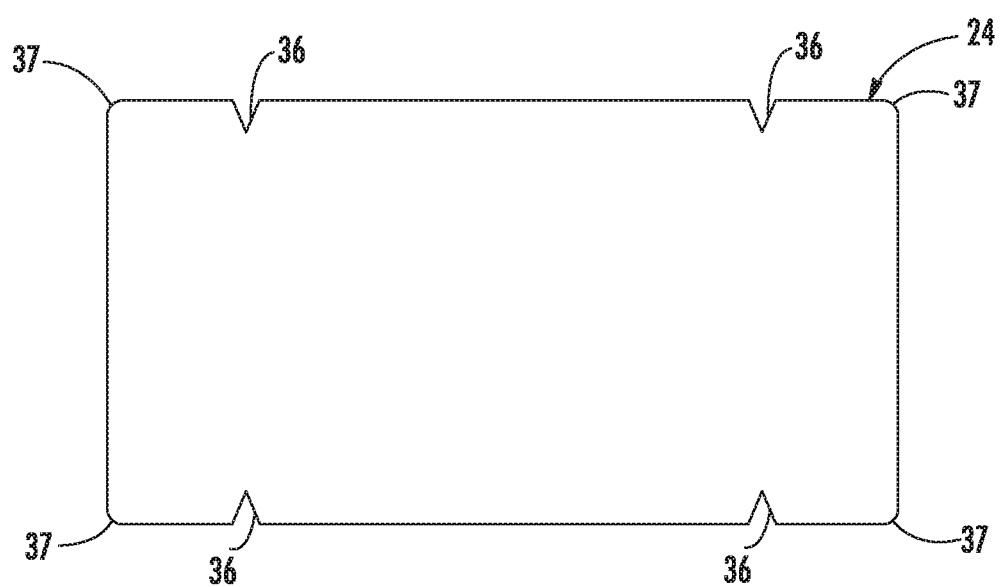
FIG. 6 illustrates a top view of another embodiment of a second or bottom panel of a dispensing assembly according to the present disclosure.

In addition, as shown in FIG. 5, the second panel 24 may include one or more corners 35 configured to abut against an internal wall of the container 12. Thus, in such embodiments, the corners 35 are configured to move along the internal wall of the container 12 as the second panel 24 is biased towards the top panel 15 of the container 12. In alternative embodiments, as shown in FIG. 6, the second panel 24 may have rounded corners 37. Thus, in such embodiments, the rounded corners 37 are configured to reduce pinching of the articles as the second panel 24 moves towards to the top panel 15, thereby reducing the articles from becoming stuck.

Referring still to FIG. 3, as shown at STEP 1 and STEP 2, the second panel 24 may be biased towards the first panel 24 via one or more flexible members 34. For example, as shown, the article dispensing component 20 includes two flexible members 34. In additional embodiments, the article dispensing component 20 may include more than two or less than two flexible members 34. Thus, the flexible members 34 are configured to allow movement of the second panel 24 toward to the first panel 22 as each article 30 is dispensed from the opening 18. It should be understood that the flexible members 34 may include any suitable members configured to bias the second panel 24 towards the first panel 24, e.g. elastic or rubber bands, springs, etc.

Referring now to FIGS. 4 and 5, the first and second panels 22, 24 may also include one or more recesses 36 configured to receive the flexible members 34. For example, as shown, each of the panels 22, 24 includes four recesses 36 configured to receive at least two flexible members 34. In additional embodiments, it should be understood that the first and second panels 22, 24 may include any number of recesses 36 to allow the dispensing assembly to operate as described herein. Further, the recesses 36 of each panel 22, 24 may have any suitable shape. For example, as shown, each of the recesses 36 has a generally triangular shape. In further embodiments, the recesses 36 may have any suitable shape, including but not limited to a square, a rectangular, or an arcuate shape. In addition, as shown in the illustrated embodiments, the recesses 36 of the first panel 22 are generally configured to align with the recesses 36 of the second panel 24. Thus, as shown in FIG. 3 at STEP 1 and STEP 2, the flexible members 34 may include elastic bands configured circumferentially around the article dispensing component 20 and within the aligned recesses 36 of the first and second panels 22, 24.

In addition, the recesses 36 in the panels 22, 24 may be configured or adjusted (e.g., moved closer together or made deeper, etc.) so as to reduce the tension provided by the flexible members 34. By reducing the tension in the flexible members 34, the dispensing assembly 10 can be more easily manufactured and assembled. In addition, the inventors of the present disclosure have discovered that the flexible members 34 do not have to provide tension to urge a full load of articles (e.g. gloves) towards the dispensing opening 18, but only needs to provide sufficient tension to urge less than a full load of articles towards the opening 18. Further, the required tension steadily decreases as the articles are dispensed from the opening 18. Alternatively and or additionally, the initial size/dimensions of the flexible members 34 and/or the material of the flexible members 34 may be altered to reduce the tension in the flexible members 34.

Figure 7:
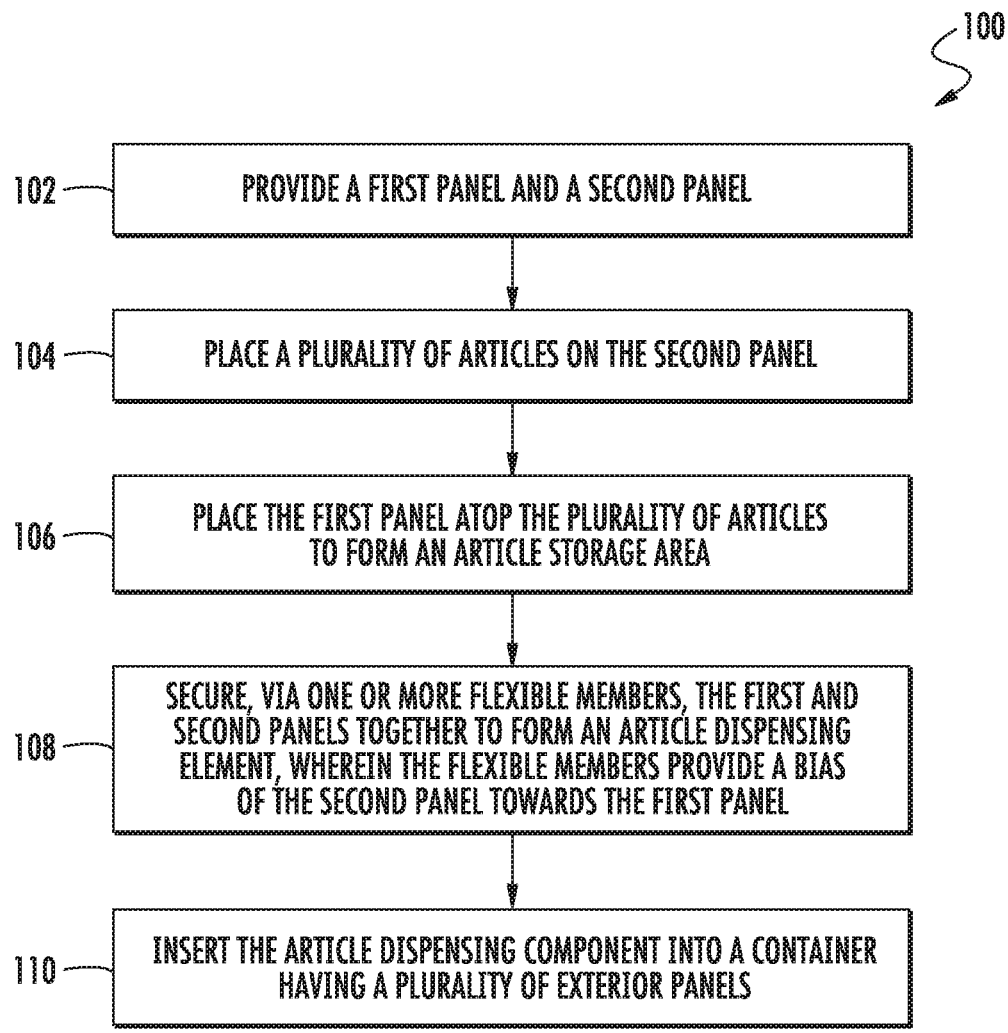
FIG. 7 illustrates a flow diagram of one embodiment of a method of manufacturing a dispensing assembly according to the present disclosure.

Referring to FIGS. 3 and 7, the present disclosure is also directed to a method 100 of manufacturing a dispensing assembly such as the dispensing assembly 10 as described herein. More specifically, as shown at 102, the method 100 includes providing a first panel and a second panel (STEP 1 of FIG. 3). At 104, the method 100 includes placing a plurality of articles on the second panel. (STEP 1 of FIG. 3). At 106, the method includes placing the first panel atop the plurality of articles to form an article storage area. (STEP 1 of FIG. 3). At 108, the method 100 includes securing, via one or more flexible members, the first and second panels together to form an article dispensing component, wherein the flexible members provide a bias of the second panel towards the first panel. (STEP 1 of FIG. 3). At 110, the method 100 includes inserting the article dispensing component into a container having a plurality of exterior panels. (STEP 2 of FIG. 3). Thus, STEP 3 illustrates one embodiment of the completed dispensing assembly 10 according to the present disclosure.

The plurality of articles as described herein is desirably a plurality of disposable articles. As used herein, the term "disposable" refers to a product that is so inexpensive that it may economically be discarded after only a single use.

Products that are "disposable" are typically intended for single use. The term "single-use" refers to a product that is intended to be used only once and is not intended to be re-used, re-conditioned, restored or repaired after that use. Such products offer advantages in clinical settings by reducing the potential for contamination or infection. In addition, these products can enhance work flow since they are not collected and assembled for reprocessing and reuse. Examples of disposable articles include disposable examination gloves, disposable facemasks and the like.

Dispensing disposable examination gloves from a package can be particularly difficult. For smaller-sized examination gloves, such as, for example, standard small or extra-small sizes, users may wish to have a smaller orifice to access the contents of the carton to prevent gloves from spilling out. The size of these gloves may be close to or not much larger than the size of the orifice. In some cases, the dimensions of the gloves may be smaller than the size of the orifice. This is particularly notable when the dispensing carton is initially opened and the contents are immediately adjacent the orifice. However, for larger-sized examination gloves, such as, for example, standard large or extra-large sizes, users may wish to have a larger orifice to provide for easier dispensing from the carton. The size of these gloves may be larger or even much larger than a typical glove dispensing orifice.

In order to improve economy, dispensing assemblies or packages are frequently larger in size to hold larger quantities of articles. When dispensing articles such as, for example, disposable examination gloves from a larger carton or package, dispensing becomes problematic after a sufficient quantity of articles (e.g., gloves) is depleted since the gloves are no longer readily accessible near the dispensing opening. Users are forced to tip the dispensing assembly or package or even insert their fingers or entire hand deep into the package to grasp and withdraw an article. The opening is typically about the same size as the user's hand, so mobility as well as vision inside the package (e.g., the chamber of the dispensing assembly) is restricted.

The present invention allows the remaining gloves of the dispensing assembly 10 to be pushed closer to the opening to enhance access to the interior of the container. This is particularly important for larger volume packages having contents that may settle or become difficult to access, especially in a health care environment.

For example, the present invention allows the user to remove a certain number of articles with each subsequent article being just as readily available as the previous article. More specifically, as the contents settle or a sufficient quantity of articles (e.g., gloves) is depleted such that the gloves are no longer readily accessible near the orifice, the present invention also allows the second panel 24 of the article dispensing component 20 to be biased towards the first panel 22 such that the articles remain close to the dispensing opening 18. Thus, the dispensing assembly 10 of the present disclosure is suitable for use with large containers.

While various patents have been incorporated herein by reference, to the extent there is any inconsistency between incorporated material and that of the written specification, the written specification shall control. In addition, while the disclosure has been described in detail with respect to specific embodiments thereof, it will be apparent to those skilled in the art that various alterations, modifications and other changes may be made to the disclosure without departing from the spirit and scope of the present disclosure.

It is therefore intended that the claims cover all such modifications, alterations and other changes encompassed by the appended claims.

What is claimed is:

1. A dispensing assembly, comprising:
a container comprising a plurality of exterior panels, the exterior panels defining an internal chamber and an opening on the container; and
an article dispensing component housed within the internal chamber, the article dispensing component comprising a first panel arranged atop and spaced apart from a second panel to form an article storage area, the article storage area configured to receive a plurality of articles,
wherein the first panel is fixed to a top panel of the container and the second panel is biased towards the first panel via one or more flexible members, the first panel comprising a plurality of first recesses, the second panel comprising a plurality of second recesses, the plurality of first recesses and the plurality of second recesses receiving the one or more flexible members, wherein a first group of the plurality of the first recesses of the first panel is aligned with a first group of the plurality of the second recesses of the second panel in a first vertical plane and a second group of the plurality of the first recesses of the first panel is aligned with a second group of the plurality of second recesses of the second panel in a second vertical plane when the first panel is arranged atop the second panel, the first and second vertical planes being parallel to each other from the plurality of first recesses to the plurality of second recesses, the first and second vertical planes being perpendicular to the second panel, wherein the first and second groups of the plurality of recesses comprise V-shaped recesses.

2. The dispensing assembly of claim 1, wherein the articles further comprise at least one of gloves, facemasks, paper products, or dust mitts.

3. The dispensing assembly of claim 1, wherein the article dispensing component is sized so as to provide an interference fit within the internal chamber of the container.

4. The dispensing assembly of claim 1, wherein the flexible members are configured to allow movement of the second panel toward to the first panel as each article is dispensed from the opening.

5. The dispensing assembly of claim 1, wherein the second panel comprises one or more rounded corners.

6. The dispensing assembly of claim 1, wherein the one or more flexible members comprise elastic bands configured circumferentially around the article dispensing component and within the aligned recesses of the first and second panels.

7. The dispensing assembly of claim 1, wherein the first panel further comprises an orifice that aligns with the opening of the container.

8. The dispensing assembly of claim 1, wherein the first panel further comprises one or more end flaps configured to form one or more side edges of the article storage area.

9. The dispensing assembly of claim 8, wherein the one or more end flaps are integral with the first panel.

10. The dispensing assembly of claim 1, wherein the exterior panels of the container further comprise opposing side panels and opposing end panels, wherein at least one of the side panels or the end panels are configured to open to allow insertion of the article dispensing component.

11. A package of articles, comprising:

a container comprising at least a top panel and a bottom panel defining an internal chamber, the top panel comprising at least one opening; and an article dispensing component housed within the internal chamber, the article dispensing component comprising a first panel and a second panel, wherein the first panel is fixed to a top panel of the container and the second panel is biased towards the first panel via one or more flexible members as each article is dispensed from the opening, the first and panel comprising a plurality of first recesses, the second panel comprising a plurality of second recesses, the plurality of first recesses and the plurality of second recesses receiving the one or more flexible members, wherein a first group of the plurality of the first recesses of the first panel is aligned with a first group of the plurality of the second recesses of the second panel in a first vertical plane and a second group of the plurality of the first recesses of the first panel is aligned with a second group of the plurality of second recesses of the second panel in a second vertical plane when the first panel is arranged atop the second panel, the first and second vertical planes being parallel to each other from the plurality of first recesses to the plurality of second recesses, the first and second vertical planes being perpendicular to the second panel, wherein the first and second groups of the plurality of recesses comprise V-shaped recesses.

12. The package of claim 11, wherein the one or more flexible members comprise elastic bands configured circumferentially around the article dispensing component and within the aligned recesses of the first and second panels.

13. The package of claim 11, wherein the first panel further comprises an orifice that aligns with the opening of the container.

14. The package of claim 11, wherein the first panel further comprises one or more end flaps configured to form one or more side edges of the article storage area.

* * * * *